United States Patent [19]
Tsubouchi

[11] Patent Number: 5,951,506
[45] Date of Patent: Sep. 14, 1999

[54] WOUND COVERING MATERIAL

[75] Inventor: Kozo Tsubouchi, Ibaraki-ken, Japan

[73] Assignees: Japan as represented by National Institute of Sericultural ans Entomological Science; Ministry of Agriculture; Forestry and Fishries, all of, Japan

[21] Appl. No.: 08/894,942

[22] PCT Filed: Jan. 23, 1997

[86] PCT No.: PCT/JP97/00144

§ 371 Date: Sep. 4, 1997

§ 102(e) Date: Sep. 4, 1997

[87] PCT Pub. No.: WO97/26927

PCT Pub. Date: Jul. 31, 1997

[30] Foreign Application Priority Data

Jan. 23, 1996 [JP] Japan ........................................ 8-28559

[51] Int. Cl.$^6$ .................................................... A61F 13/00
[52] U.S. Cl. .................................. 602/48; 602/6; 602/42; 602/43; 106/124.1
[58] Field of Search .................................... 602/48, 6, 42, 602/43; 106/124.1

[56] References Cited

U.S. PATENT DOCUMENTS

| 4,325,741 | 4/1982 | Otoi et al. | 106/308 |
| 5,252,285 | 10/1993 | Lock | 264/202 |
| 5,263,983 | 11/1993 | Yoshizato et al. | 424/428 |

FOREIGN PATENT DOCUMENTS

| 56-34349 | 4/1981 | Japan . |
| 56-40156 | 4/1981 | Japan . |
| 2109570 | 4/1990 | Japan . |
| 2233128 | 9/1990 | Japan . |

*Primary Examiner*—Richard J. Apley
*Assistant Examiner*—Kelvin Hart
*Attorney, Agent, or Firm*—Lorusso & Loud

[57] ABSTRACT

A wound covering material is provided which can smoothly accelerate repair of a skin defect and which can be readily removed without causing the repaired skin to be removed together therewith. The wound covering material includes a film containing a non-crystalline fibroin.

8 Claims, No Drawings

WOUND COVERING MATERIAL

TECHNICAL FIELD

The present invention relates to a wound covering material.

BACKGROUND ART

A covering material to be applied to a skin defect as an artificial skin is called a wound covering material. A pig skin, chitin and so on have already been developed for such a wound cover. These materials, however, have drawbacks in that a new skin developing under the artificial skin may be removed as the artificial skin is being removed. Further, there has recently been developed a wound covering material referred to as "Dioactive CGF" and this wound covering material is less likely to remove the new skin developing under the artificial skin, upon removal of the wound covering material. This wound covering material, however, is said to be slower in the speed of forming a new skin below, as compared to a pig skin.

DISCLOSURE OF INVENTION

It is an object of the present invention to provide a wound covering material that can smoothly accelerate the growth of new skin thereunder and that can be removed without removal of the new skin therewith.

As a result of extensive studies and research to achieve the object as described hereinabove, the present invention provides a wound covering material comprising a non-crystalline fibroin film.

The wound covering material (hereinafter referred to sometimes as a "covering material") according to the present invention can be prepared by using an aqueous fibroin solution as a raw material and processing it into a film.

For the preparation of an aqueous fibroin solution, a silky substance is purified by removing sericin. The silky substance may include, for example, cocoons, cocoon thread, silk yarn, silk cloth and waste thereof. The purification of the silky substance may be carried out, for example, by boiling the silky substance in an enzyme or in an aqueous solution of an alkali such as sodium carbonate, sodium hydrogen carbonate or the like, washing the resulting silky substance with water, and immersing it in warm water, thereby causing chemical substances such as sericin, sodium carbonate and so on to be eluted and removing them. It is preferred that the purified silky substance is then sterilized with ethylene oxide gas, in an autoclave or by any other means.

The silky substance purified in the way as described hereinabove is then dissolved in pure water containing a dissolution aid. The dissolution aid to be employed in this case may include, for example, an acid, a neutral salt-such as calcium chloride, lithium bromide or the like or ethanol.

The aqueous solution in which the silky substance is dissolved is subjected to dialysis by means of a semipermeable membrane tube or the like, thereby yielding an aqueous fibroin solution from which the dissolution aid has been removed.

The concentration of fibroin in the aqueous fibroin solution may be 2% by weight or higher, preferably 5% by weight or higher, although it is usually in the range of from 5% to 20% by weight. The amount of impurities other than fibroin in the aqueous fibroin solution may be 0.01% by weight or lower, preferably 0.0001% by weight or lower. In this case, there is the possibility that sericin, chlorine or the like may be contained as impurities.

The process of forming the aqueous fibroin solution into a film may comprise casting the aqueous fibroin solution on a flat and smooth surface of a solid member and removing the water contained therein by evaporating it. It is of great importance in this case that the resulting fibroin film is not made crystalline and that it becomes a substantially non-crystalline film. In order to achieve this, it is preferred to adjust the speed of removing the water by evaporation from the aqueous fibroin solution in the process of film formation and it is possible to prevent crystallization of the resulting film by increasing the speed of the evaporation of the water.

The crystallization of the fibroin film occurs in the process of drying the aqueous fibroin solution when it takes a long time to dry while the concentration of the aqueous fibroin solution is 30% or higher. In order to prevent the crystallization of the fibroin film, the aqueous fibroin solution may be dried at a reduced pressure of 0.5 atmospheres or lower, preferably 0.1 atmospheres or lower. When the drying is carried out at ambient pressure, it is necessary to control the temperature, humidity and wind velocity of gaseous fluid such as air or inert gas (nitrogen gas or the like) in the drying chamber. The temperature at which the aqueous fibroin solution is formed into a film may range from 0° C. to 50° C., preferably from 10° C. to 30° C. The relative humidity RH of air or such inert gas may range from 40% to 90%, preferably from 50% to 80%. It is preferred that the aqueous fibroin solution is formed into a film by bringing a film of the fibroin solution cast on the solid surface into contact with air or the inert gas (nitrogen gas or the like) having a temperature in the range of from 0° C. to 50° C., preferably from 10° C. to 30° C. at a wind velocity of 5 cm per second or higher, preferably from 10 cm per second to 30 cm per second. When it is intended to prepare a fibroin film having a film thickness of 30 $\mu$m or thicker, particularly in the range of from 40 to 60 $\mu$m, it is preferred that the wind velocity of the air or inert gas be 10 cm per second or higher or the relative humidity be set to be approximately 30% RH at a wind velocity of about 10 cm per second or lower, thereby preventing the crystallization of the resulting fibroin film. It is preferred that the fibroin film have a solubility in water of 60% or more at room temperature.

For the fibroin film to be employed as a covering material in accordance with the present invention, the film thickness may be in the range of from 10 $\mu$m to 100 $\mu$Am. The water contents of the resultant film may be in the range of from 3% to 16% by weight, preferably from 5% to 13% by weight. The resulting fibroin film may be laminated on any other material such as a support, if desired.

When the covering material is actually used, it is preferred to sterilize it with ethylene oxide gas prior to use.

EXAMPLES

The present invention will be described in more detail by way of example.

Example (1) Preparation of a Raw Material

Raw silk yarn was boiled in a 0.5% (by weight) sodium carbonate aqueous solution for 1 hour, washed with water and immersed in warm water at 60° C. for 30 minutes to thereby remove sericin and sodium carbonate. The resulting silk yarn was sterilized in an autoclave and employed as a raw material for preparing a fibroin film.

(2) Dissolution of Silk Yarn

The purified silk yarn prepared in the step (1) above was dissolved in an aqueous solution consisting of water, calcium chloride and ethanol (molar ratio=1:2:8). The weight ratio of the silk yarn with respect to the aqueous solution was adjusted to be 1:7. The resultant aqueous solution was filled into a cellulose tube (a semipermeable membrane) and subjected to dialysis with pure water, thereby yielding an aqueous fibroin solution. The concentration of fibroin in the resultant aqueous fibroin solution was found to be approximately 7% by weight.

(3) Preparation of a Fibroin Film

The resulting aqueous fibroin solution was cast in a given area on a flat plastic plate and dried while feeding air at a wind velocity of from 20 to 40 cm per second in a chamber having a temperature of 20° C. and a relative humidity of 65% RH. Although the film thickness of the fibroin film may vary with the concentration and the amount of the aqueous fibroin solution and the area of a film surface to be dried, it is set to become 10 μm or thicker in this case. Further, the wind velocity is increased as the resulting film becomes thicker because the film becomes more crystalline as it thickens.

(4) Properties of the Fibroin Film

From the fact that an X-ray diffraction photograph of the resultant fibroin film shows an amorphous halo, it is confirmed that the fibroin is non-crystalline. In order to determine solubility of the resulting fibroin film in water (at room temperature), the fibroin film was dissolved in water at room temperature and, as a result, it is found that the resultant fibroin film dissolved almost fully in water within several minutes. From this result, it is further confirmed that the resulting fibroin film is substantially non-crystalline.

Furthermore, in order to determine an interaction of the fibroin film with blood, one droplet of blood was dropped onto the film. As a result, the blood was absorbed within one minute and the film became swollen. This indicates that the resulting non-crystalline fibroin film has a good interaction with a body liquid and the body liquid is adsorbed thereon very well while water is likely to be evaporated therethrough.

(5) Functions as a Wound Covering Material

In order to determine the functions of the non-crystalline fibroin film as a wound covering material, the film was applied to a fire burn site after it has been sterilized with ethylene oxide gas. As a result, it is found that the film absorbed the body liquid and that the water evaporated from its surface, thereby keeping the wound site in a dry state. It is further found that the resulting film allowed a new skin to be created at the wound site, even when it had been applied to the site without exchange for a week. From this result, it is confirmed that the fibroin film has utility as an artificial skin.

The wound covering material according to the present invention presents the advantages that the repair of a skin defect and the creation of a new skin can be accelerated by covering the surface of the wound with this wound covering material as an artificial skin and that the film can be removed without removal of the repaired skin or the new skin underneath. Further, when the wound covering material according to the present invention is applied to the skin defect, it has the further advantage that it does not require exchange over a long period of time.

I claim:

1. A wound covering material comprising a film containing a non-crystalline fibroin.

2. A wound covering material as claimed in claim 1, wherein said film containing non-crystalline fibroin has a water content of from 3% to 16% by weight.

3. A wound covering material as claimed in claim 1, wherein said film containing non-crystalline fibroin has a thickness of from 10 μm to 100 μm.

4. A wound covering material as claimed in claim 2, wherein said film containing non-crystalline fibroin has a thickness of from 10 μm to 100 μm.

5. A method of treating a skin wound comprising covering the skin wound with a film containing non-crystalline fibroin so that the film containing the non-crystalline fibroin is in contact with the skin wound.

6. A method as claimed in claim 5 wherein said film containing non-crystalline fibroin has a water content of from 3% to 16% by weight.

7. A method as claimed in claim 5 wherein said film containing non-crystalline fibroin has a thickness of from 10 μm to 100 μm.

8. A method as claimed in claim 6 wherein said film containing non-crystalline fibroin has a thickness of from 10 μm to 100 μm.

* * * * *